(12) United States Patent
Deppert et al.

(10) Patent No.: US 6,649,353 B2
(45) Date of Patent: *Nov. 18, 2003

(54) METHOD FOR INFLUENCING THE P53 LINKAGE TO TARGET GENES

(76) Inventors: Wolfgang Willi Deppert, Im Hain 14, Hamburg (DE), D-22359; Ella Kim, Heinrich-Petta-Institut Martinistrasse 52, Hamburg (DE), D-20251

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/485,791
(22) PCT Filed: Aug. 7, 1998
(86) PCT No.: PCT/DE98/02326
§ 371 (c)(1), (2), (4) Date: May 2, 2000
(87) PCT Pub. No.: WO99/08712
PCT Pub. Date: Feb. 25, 1999

(65) Prior Publication Data
US 2003/0032009 A1 Feb. 13, 2003

(30) Foreign Application Priority Data
Aug. 14, 1997 (DE) .................................. 197 35 221

(51) Int. Cl.[7] .................... G01N 33/53; G01N 33/68
(52) U.S. Cl. .................................. 435/7.1; 435/6
(58) Field of Search ................... 435/6, 7.1; 514/44

(56) References Cited

FOREIGN PATENT DOCUMENTS

| WO | 94/12202 | * 6/1994 |
|---|---|---|
| WO | WO 97/11367 | 3/1997 |
| WO | WO 97/14794 | 4/1997 |

OTHER PUBLICATIONS

Verma et al (1997) Nature 389:239–242.*
Palù et al (1999) J. Biotechnol. 68: 1–13.*
Luo et al (2000) Nature Biotechnology 18:33–37.*
Freifelder (1987) Molecular Biology, 2nd Edition, Jones and Bartlett Publishers, Boston. p. 111.*
Hainaut et al (1995) Oncogene 10:27–32.*
Hall et al (1995) Oncogene 10:561–567.*
White (1996) Genes Dev. 10:1–15.*
Nagaich et al (1997) J. Biol. Chem. 272:14842–14849.*
Hansen et al., 1996, "Allosteric regulation of the thermostability and DNA binding activity of human p53 by specific interacting proteins," *J. Biol. Chem.* 271(7):3917–3924.
Kim et al., 1997, "DNA–conformation is an important determinant of sequence–specific DNA binding by tumor suppressor p53," *Oncogene* 15(7):857–869 (Published erratum appears in *Oncogene*, 1997, 15(19):2385.

* cited by examiner

*Primary Examiner*—Remy Yucel
*Assistant Examiner*—Bronwen M. Loeb
(74) *Attorney, Agent, or Firm*—Pennie & Edmonds LLP

(57) ABSTRACT

The invention relates to a method for influencing the p53 binding to a target gene, wherein the conformations of p53 and the target gene are coordinated especially by means of conformation modulators and the binding of p53 can be directly or indirectly detected.

15 Claims, 4 Drawing Sheets

(SEQ ID NO: 5)
```
      AT
      CG
     A C
      GC
      AT
      ta
5'-gccgccagct tcgaccgccg
   cggcggtcga agctggcggc
         Hu/La-2
```

(SEQ ID NO: 6)
```
      TA
      CG
     C A
      GC
      TA
      AT
      CG
     A C
      GC
      AT
      ta
```

(SEQ ID NO: 8)
```
5'-gccgccagct tcgaccgccg
   cggcggtcga agctggcggc
         Hu/La-1
```

(SEQ ID NO: 7)
```
5'-agct tAGACATGCCTAGACATGCCT
    tcgaaTCTGTACGGATCTGTACGGA
```

(SEQ ID NO: 9)
Hu/La-du/ds

FIG. 3

METHOD FOR INFLUENCING THE P53 LINKAGE TO TARGET GENES

This is a national phase filing of the Application No. PCT/DE98/02326, which was filed with the Patent Corporation Treaty on Aug. 7, 1998, and is entitled to priority of the German Patent Application 197 35 221.9, filed Aug. 14, 1997.

I. FIELD OF THE INVENTION

The present invention relates to a method for influencing the p53 binding to target genes.

II. BACKGROUND OF THE INVENTION p53 is a protein present in animal and human cells and is referred to as a "guardian of the genome." p53 is a sequence-specific transactivator which is activated in the case of DNA damage. In this form, p53 binds to promoters of target genes and activates the transcription thereof. This causes growth stand-still of the cells and subsequent repair of the DNA damage and cell death, respectively.

It has turned out that p53 has lost its transactivator activity in many tumors. This is often due to the fact that the binding of p53 to the promoters of target genes is disturbed or it is not the desired target genes that are regulated.

Therefore, it is the object of the present invention to provide a product by which it is possible to influence the binding of p53 to target genes.

III. SUMMARY OF THE INVENTION

The invention relates to a method for influencing the p53 binding to a target gene, wherein the conformations of p53 and the target gene are coordinated especially by means of conformation modulators and the binding of p53 can be directly or indirectly detected.

IV. BRIEF DESCRIPTION OF THE DRAWINGS

FIG. 1 shows the DNA conformations of oligonucleotides (SEQ ID NOS: 1–3) which contain on their termini the p53 binding sequence RGC. SEQ ID NO: 2 is in conformation II (i.e., B DNA conformation), while SEQ ID NOS:1 and 3 are in conformation I and III (i.e., non-B DNA conformation). To demonstrate the different conformations, RGC containing oligonucleotides are subjected to an annealing reaction with an oligonucleotide, designated "Lock," (SEQ ID NO:4) that has complementary sequences to the sequence of the RCG sequences on the termini of SEQ ID NOS:1–3. The autoradiograph of a polyacrylamid gel is shown on which the the various reaction products has been separated. Lanes 2, 4, and 6 show the annealing product of SEQ ID NOS:1, 2, and 3, respectively, with "Lock" (SEQ ID NO:4) where "Lock" was radioactively labeled. Lane 1 shows radioactively labeled "Lock" as control. Lane 8 shows radioactively labeled RCG containing oligonucleotides as control.

FIG. 2 shows the DNA binding of p53 to RCG containing oligonucleotides (SEQ ID NOS:1, 2, and 10). Lanes 3 and 4 show binding to RCG 1a/ss (SEQ ID NO:1), lanes 5 and 6 show the binding to RCG 1b/ss (SEQ ID NO:10), and lanes 7 and 8 show the binding to RCG dm/ss (SEQ ID NO:2). Lanes 1 and 2 represent controls.

FIG. 3 shows the DNA conformations of oligonucleotides which contain p53 binding sequences of the sequence found by Hupp (SEQ ID NOS:5–6) annealed to Lock-2 (SEQ ID NO:8), and (SEQ ID NO:7) annealed to (SEQ ID NO:9).

V. DETAILED DESCRIPTION OF THE INVENTION

Figure 1:
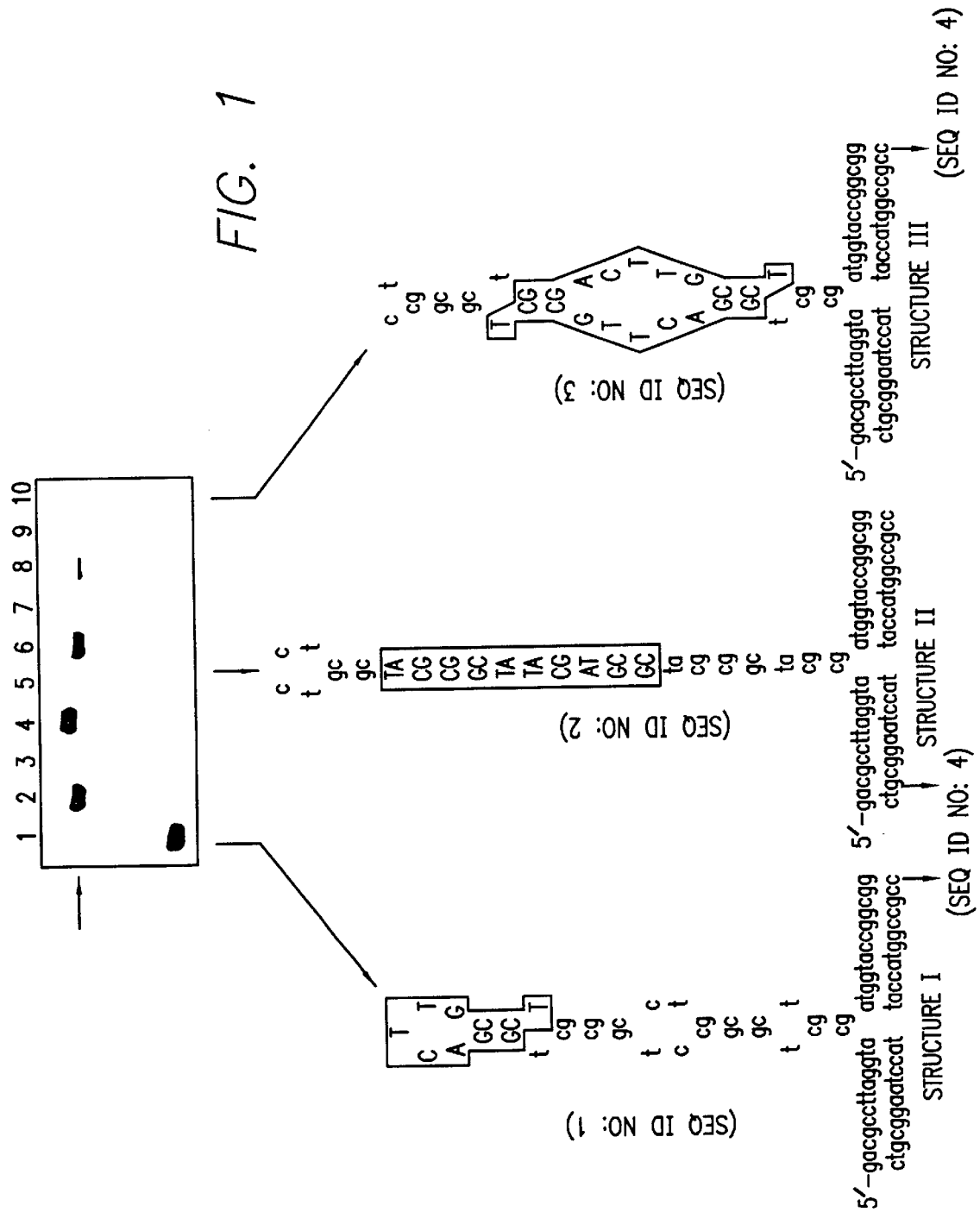

It is the object of the present invention to provide a product by which it is possible to influence the binding of p53 to target genes.

According to the invention this is achieved by the subject matters defined in the claims.

Thus, the subject matter of the present invention relates to a method of influencing the binding of p53 to a target gene in which the conformations of p53 and the target gene are coordinated, particularly by means of conformation modulators, and the binding of p53 is detected directly or indirectly.

The present invention is based on the applicant's insight that p53 binding sequences in the promoters of target genes can be present not only in the "ordinary" B-duplex DNA conformation but also in non-B DNA conformations (e.g., cruciate). The applicant also discovered that p53 identifies its binding sequences in both the B-duplex DNA conformation and in the non-B DNA conformations. However, the identification differs depending on the conformation of p53.

According to the invention these insights are used to influence to binding of p53 to target genes by coordinating the conformations of p53 and the target genes, particularly by means of conformation modulators, and detecting the p53 binding directly or indirectly.

The expression "p53" comprises a p53 of any kind and origin. It can have a wild-type sequence or be a mutated p53. The latter is preferably a p53 with mutated ability of DNA binding. p53 can also be present in the form of a fragment of p53 which is responsible for the DNA binding. In addition, p53 can be present in the form of a fusion polypeptide. Like any other p53 it can also be present in the form of a vector coding for it.

The term "target genes" comprises genes of any kind and origin the expression of which is regulated by p53. Examples of such genes are RGC, MCK, mdm2, cyclin G, synthetic p53 reporter genes, p21 and bax, p21 and particularly bax being preferred. p21 is held responsible for the growth stand-still of the cell caused by p53 and bax is held responsible for the cell death caused by p53. In particular, the expression "target genes" comprises the promoter sequences thereof and more particularly p53 binding sequences thereof. The target genes may be present in any DNA conformation. They can be present in cells, particularly tumor cells, or occur in isolated fashion. The target genes can also be present in connection with further sequences, particularly with those coding for a reporter protein.

The expression "conformation modulators" comprises substances of any kind which can cause a conformational change of a nucleic acid. In particular, substances are concerned which can convert a DNA from the B-duplex DNA conformation into a non-B DNA conformation or vice versa. Examples of such substances are intercalating substances. The expression "conformation modulators" also comprises substances of any kind which can effect a conformational change of p53. Examples of such substances are those which can modify the carboxy-terminal regulator region of p53, e.g., antibody pAB 421.

The expression "direct or indirect detection of p53 binding" comprises any detection for such a binding. Examples of a direct detection comprise methods by means of which the p53 binding to DNA can be shown. Indirect detections include methods by means of which it is possible to show the consequences of a p53 DNA binding, e.g., the regulation of the expression of reporter genes and/or biological consequences, such as the growth stand-still of cells or the death thereof.

A method according to the invention can be carried out as usual. For example, p53 binding sequences in the B-duplex DNA conformation and in a non-B DNA conformation, respectively, can be incubated with p53 and optionally conformation modulators and the DNA binding of p53 is detected directly. It is possible to incubate cells, particularly tumor cells, having disturbed DNA binding of p53 with conformation modulators and upon irradiation of the cells the DNA binding of p53 is detected indirectly via the growth stand-still and the death of the cells, respectively.

By means of the present invention it is possible to influence the p53 binding to target genes. This can be used to correct a disturbed DNA binding of p53, which often exists in tumor cells. Furthermore, the DNA binding specificity of p53 can be influenced so as to regulate or control certain desired target genes. Thus, the present invention can be used at least as an accompanying treatment measure to combat tumoral diseases.

The present invention also offers the possibility of discovering substances which can be suitable as conformation modulators of p53 and/or its target genes. For this purpose, the method according to the invention is carried out to the effect that in place of known conformation modulators unknown ones are used and the known conformation modulators are optionally used as controls.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1 p53 Binding To A Target Gene (a) p53 Binding to p53 Binding Sequences of RGC p53 was isolated as usual from Sf9 insect cells which were infected with recombinant wild type p53-expressing baculoviruses. p53 had a purity of over 80% in an SDS polyacrylamide gel. p53 was used in a binding reaction with oligonucleotides. For preparing these oligonucleotides, the below oligonucleotides were used as a basis:

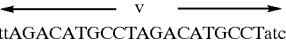

| Hu/La-1 | ←——— v ———→ | (SEQ ID NO:6) |
| 5'-gccgccagcttAGACATGCCTAGACATGCCTatcgaccgccg-3' |
| Hu/La-2 | ←——— v ———→ | (SEQ ID NO:5) |
| 5'-gccgccagcttAGACATGCCTatcgaccgccg-3' |
| Hu/La-du | ←——— v ———→ | SEQ ID NO:7) |
| 5'-agcttAGACATGCCTAGACATGCCTa-3' |

These oligonucleotides contain 1–2 "halfsites" of the p53 binding sequences of RGC and in each case identical terminal sequences at their 5' ends and 3' ends. The oligonucleotides were used in an "annealing" reaction with the below oligonucleotide which has complementary sequences with respect to the terminal sequences:

Lock 5'-ccgcggtaccattacctaaggcgtc-3'   (SEQ ID NO:4)

Oligonucleotides were obtained which are present in the duplex-B DNA conformation (structure II) and in the non-B DNA conformations, respectively (structures I and III, respectively). See, FIG. 1. These oligonucleotides were terminally labeled radioactively and used in the binding reaction with p53. The reaction lasted 30 minutes at room temperature. The reaction products were subjected to polyacrylamide gel electrophoresis.

Figure 2:
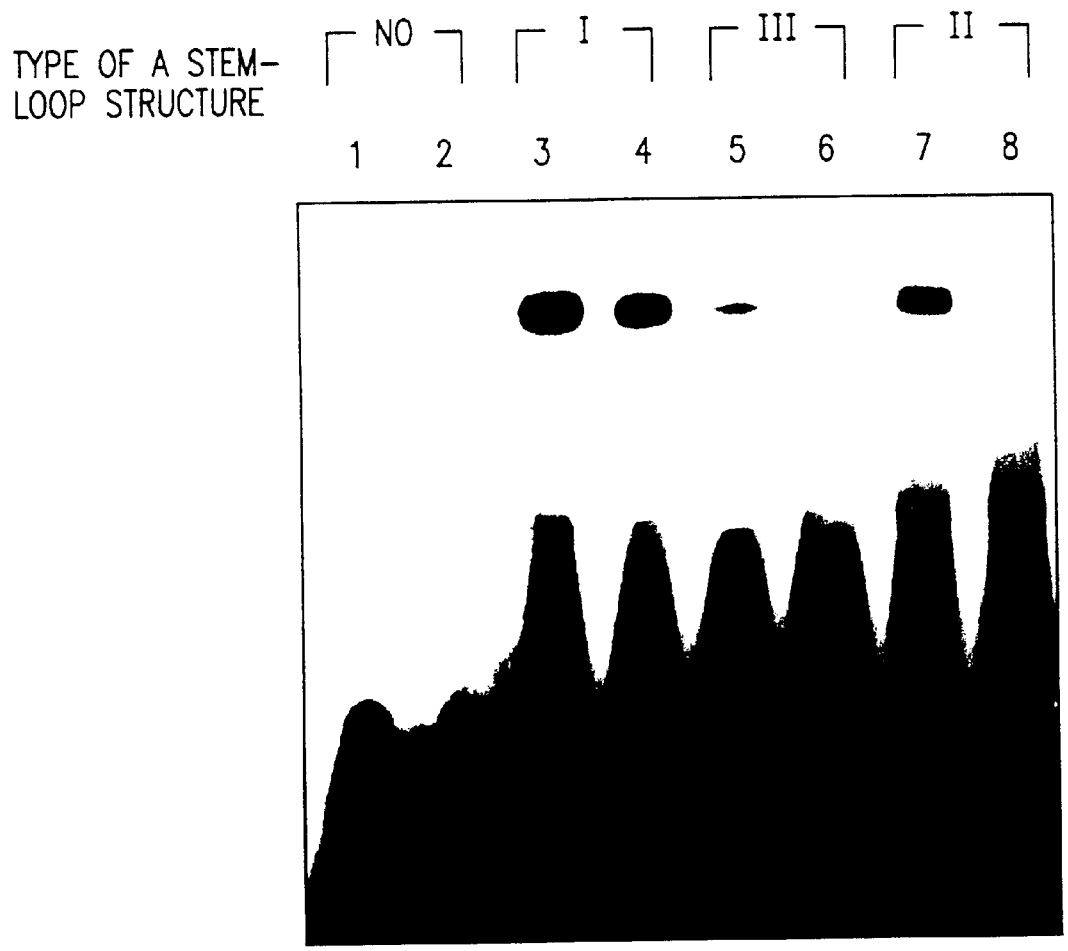

It turned out that p53 binds to the oligonucleotides of the three DNA conformations, although to differing degrees. The strongest bond is found in the case of a non-B DNA conformation (structure I), while the bond to the duplex-B DNA conformation (structure II) and to another non-B DNA conformation (structure III), respectively, is weaker. See, FIG. 2. Thus, it becomes evident that the p53 binding to a target gene can be influenced by a conformational change of the target gene.

(b) p53 Binding to p53 Binding Sequences of the Hupp Sequence

In accordance with the description of (a), p53 was used in a binding reaction with oligonucleotides. For the preparation thereof, the below oligonucleotides were used as a basis:

RGC - 1 b/ss  5'-gacgccttaggtagggccctGGACTTGCCTcccgggatggtaccgcgg-3'  (SEQ ID NO:10)

RGC - 1 a/ss  ←————— v —————→  (SEQ ID NO:1)
5'-gacgccttaggtacctggcctgcctGGACTTGCCTggcctgcctggatggtaccgcgg-3'

RGC-dm/ss  ←——————— v ———————→  (SEQ ID NO:2)
5'-gacgccttaggtacctgcctGGACTTGCCTggtcctccAGGCAAGTCCaggcaggatggtaccgcgg-3'

They contain 1–2 "halfsites" of the p53 binding sequences discovered by Hupp. These p53 binding sequences distinguish themselves in that p53 can bind thereto only after its activation by the antibody PAb 421. The oligonucleotides were used in an "annealing" reaction with the oligonucleotide "lock" indicated in (a). (SEQ ID NO:4). Oligonucleotides were obtained which are present in the duplex-B DNA conformation (Hu/La-du/ds) (SEQ ID NO:7) and in the non-B DNA conformations, respectively (Hu/La-2 (SEQ ID NO:5) and Hu/La-1 (SEQ ID NO:6), respectively). See, FIG. 3.

Figure 4:
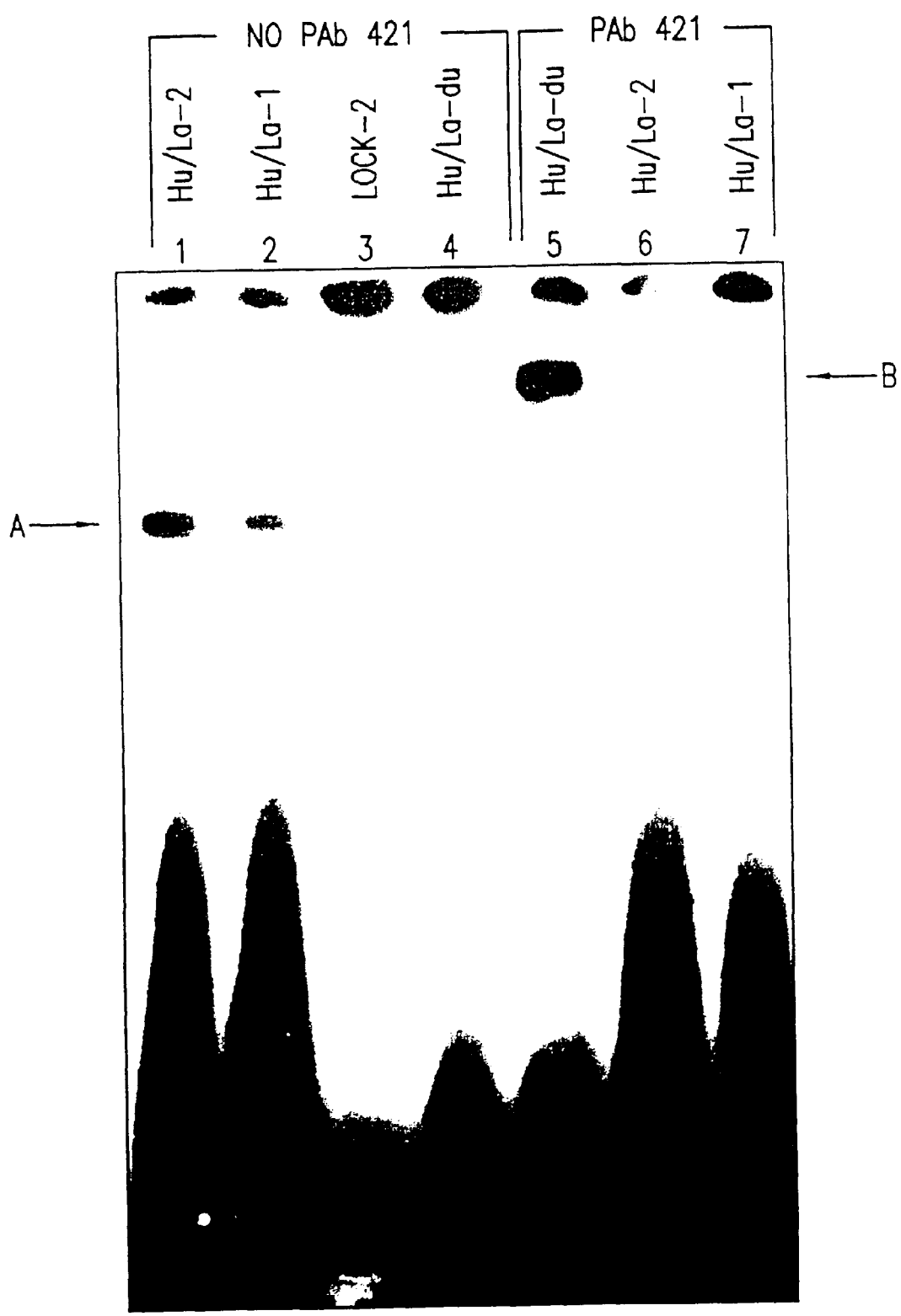
FIG. 4 shows the DNA binding of p53 to oligonucleotides by p53 binding sequences of the Hupp sequences (SEQ ID NOS:5–7), the oligonucleotides having various DNA conformations. (A) indicates the absence, (B) the presence of antibody pAb421.

It turned out that p53 binds to the oligonucleotides of the three DNA conformations, although to differing degrees. p53 binds to the oligonucleotide in the duplex-B DNA conformation only after the activation of p53 by the PAb 421 antibody, while its binding to non-B DNA conformations takes place without modification of p53. See, FIG. 4. On the other hand, the binding of PAb 421 to p53 effects an inhibition of the p53 binding to this oligonucleotide in the non-B DNA conformation. Hence it becomes evident that the p53 binding to a target gene can be influenced by conformational changes of the target gene and of p53.

What is claimed:

1. A method for identifying a conformation modulator of a p53 target nucleic acid sequence, comprising:

(a) providing a p53 molecule and a p53 target nucleic acid sequence;

(b) exposing said p53 molecule and said p53 target nucleic acid sequence to a candidate substance; and (c) identifying that said candidate substance is a conformation modulator of a p53 target nucleic acid sequence by comparing binding of said p53 molecule to said p53 target nucleic acid sequence in the presence of said candidate substance to binding of said p53 molecule to said p53 target nucleic acid sequence in the absence of said candidate substance.

2. The method of claim 1, wherein said conformation modulator is a substance that converts the p53 target nucleic acid sequence from B-duplex formation to a non B-duplex formation.

3. The method of claim 1, wherein said conformation modulator is an intercalating substance.

4. The method of claim 1, wherein said p53 target nucleic acid sequence is p21 or bax.

5. The method of claim 1, wherein said p53 molecule is a truncated form of p53, said truncated form of p53 having the ability to bind a p53 target nucleic acid sequence.

6. The method of claim 1, wherein said p53 molecule is a fusion polypeptide.

7. The method of claim 1, wherein binding of said p53 molecule to said p53 target nucleic acid sequence is detected directly.

8. The method of claim 1, wherein binding of said p53 molecule to said p53 target nucleic acid sequence is detected indirectly.

9. The method of claim 1, 2, or 3, wherein said p53 is a mutated p53.

10. The method of claim 1, 2, or 3, wherein said p53 molecule is a wild-type p53 molecule.

11. The method of claim 1, 2, or 3, wherein said p53 target nucleic acid sequence regulates the expression of a synthetic reporter gene.

12. The method of claim 9, wherein said mutation of p53 affects the DNA binding affinity of said mutated p53.

13. The method of claim 9, wherein binding of said p53 molecule to said p53 target nucleic acid sequence is detected by the expression of a reporter gene, wherein said p53 target nucleic acid sequence regulates the expression of said reporter gene.

14. The method of claim 8, wherein binding of said p53 molecule to said p53 target nucleic acid sequence is detected by the biological consequence of p53 binding to said p53 target nucleic acid sequence, wherein said biological consequence is cell growth arrest.

15. The method of claim 1, wherein binding of said p53 molecule to said p53 target nucleic acid sequence is detected by the biological consequence of p53 binding to said p53 target nucleic acid sequence, wherein said biological consequence is cell death.

* * * * *

SEQUENCE LISTING

```
<160> NUMBER OF SEQ ID NOS: 10

<210> SEQ ID NO 1
<211> LENGTH: 58
<212> TYPE: DNA
<213> ORGANISM: Artificial Sequence
<220> FEATURE:
<223> OTHER INFORMATION: Description of Artificial Sequence: p53
      binding oligonucleotide RGC-1a/ss

<400> SEQUENCE: 1
gacgccttag gtacctggcc tgcctggact tgcctggcct gcctggatgg taccgcgg        58

<210> SEQ ID NO 2
<211> LENGTH: 67
<212> TYPE: DNA
<213> ORGANISM: Artificial Sequence
<220> FEATURE:
<223> OTHER INFORMATION: Description of Artificial Sequence: p53
      binding oligonucleotide RGC-dm/ss

<400> SEQUENCE: 2
gacgccttag gtacctgcct ggacttgcct ggtcctccag gcaagtccag gcaggatggt      60
accgcgg                                                                67

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: p53
      binding oligonucleotide RGC in conformation III

<400> SEQUENCE: 3
gacgccttag gtacctggac ttgcctggcc tgcctggact tgcctatggt accggcgg        58

<210> SEQ ID NO 4
<211> LENGTH: 25
<212> TYPE: DNA
<213> ORGANISM: Artificial Sequence
```

```
<220> FEATURE:
<223> OTHER INFORMATION: Description of Artificial Sequence: "Lock"
      annealing oligonucleotide

<400> SEQUENCE: 4
ccgcggtacc attacctaag gcgtc                                              25

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Binding
      oligonucleotide Hu/La-2

<400> SEQUENCE: 5
gccgccagct tagacatgcc tatcgaccgc cg                                      32

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:Binding
      oligonucleotide Hu/La-1

<400> SEQUENCE: 6
gccgccagct tagacatgcc tagacatgcc tatcgaccgc cg                           42

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:Binding
      oligonucleotide Ha/La-du

<400> SEQUENCE: 7
agcttagaca tgcctagaca tgccta                                             26

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: "Lock-2"
      annealing oligonucleotide

<400> SEQUENCE: 8
cggcggtcga agctggcggc                                                    20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: annealing
      oligonucleotide

<400> SEQUENCE: 9
tcgaatctgt acggatctgt acgga                                              25

<210> SEQ ID NO 10
<211> LENGTH: 48
<212> TYPE: DNA
<213> ORGANISM: Artificial Sequence
<220> FEATURE:
```

```
<223> OTHER INFORMATION: Description of Artificial Sequence: p53
      binding oligonucleotide RGC-1b/ss

<400> SEQUENCE: 10
gacgccttag gtagggccct ggacttgcct cccgggatgg taccgcgg         48
```